United States Patent [19]
Mullen et al.

[11] Patent Number: 5,679,565
[45] Date of Patent: Oct. 21, 1997

[54] METHOD OF PRESERVING PANCREATIC ISLETS

[75] Inventors: Yoko Mullen, Sherman Oaks, Calif.; Takashi Kenmochi, Hanamigawaku, Japan

[73] Assignee: The Regents of the University of California, Oakland, Calif.

[21] Appl. No.: 420,005

[22] Filed: Apr. 10, 1995

[51] Int. Cl.$^6$ .................................... C12N 5/00; C12N 5/06
[52] U.S. Cl. .................................. 435/240.1; 435/260
[58] Field of Search ........................... 210/647; 435/1.1, 435/1.2, 1.3, 2, 183, 240.1, 260; 424/697, 709

[56] References Cited

U.S. PATENT DOCUMENTS

| | | | |
|---|---|---|---|
| 4,797,213 | 1/1989 | Parisius et al. | 210/651 |
| 4,798,824 | 1/1989 | Belzer et al. | 514/60 |
| 4,868,121 | 9/1989 | Scharp et al. | 435/268 |
| 4,873,230 | 10/1989 | Belzer et al. | 514/60 |
| 4,879,283 | 11/1989 | Belzer et al. | 514/60 |
| 5,200,398 | 4/1993 | Strasberg et al. | 514/60 |
| 5,322,790 | 6/1994 | Scharp et al. | 435/268 |
| 5,328,821 | 7/1994 | Fisher et al. | 435/240.1 |
| 5,328,844 | 7/1994 | Moore | 435/240.2 |
| 5,405,742 | 4/1995 | Taylor | 435/1.2 |
| 5,411,883 | 5/1995 | Boss et al. | 435/240.2 |
| 5,514,536 | 5/1996 | Taylor | 435/1.2 |

FOREIGN PATENT DOCUMENTS

WO91/04318  4/1991  WIPO.

OTHER PUBLICATIONS

"Automated Method for Isolation of Human Pancreatic Islets," C. Ricordi, P.E. Lacy, E.H. Finke, B.J. Olack, and D.W. Scharp, Diabetes, vol. 37, Apr. 1988, pp. 413–420.

"A Comparison of Four Solutions for Cold Storage of Pancreatic Islets," V.D.A. Delfino, D.W.R. Gray, C. K. Leow, S. Shimizu, D.J.P. Ferguson, and P. J. Morris, Transplantation, vol. 56, No. 6, Dec. 1993, pp. 1325–1330.

"Improved Yield and Survival of Porcine Islets With Newly Developed Lap–1 Solution," T. Kenmochi, M. Miyamoto, Y. Nakagawa, S. Une, P.Y. Benhamou, and Y. Mullen, Transplantation Proc., vol. 26, No. 6, Dec. 1994, pp. 4012.

"Comparison of Islet Isolation Techniques in Dogs: Over 90% Purified Islets Using UW Solution" M.P.M. van der Burg, H.G. Gooszen, R.J. Ploeg, J.P. Scherft, M.J. Field, O.R. Guicherit, J.L. Terrpstra, F.T. vande Woude, M. Frölich, and J.A. Bruijn, Transplantation Proceedings, vol. 22, No. 2, Apr. 1990, pp. 795–796.

"Metabolic Control After Autotransplantation of Highly Purified Canine Pancreatic Islets Isolated in UW Solution," M.P.M. vander Burg, O.R. Guicherit, R.J. Ploeg, M. Frolich, J.A. Bruijn, J.P. Scherft, and H.G. Gooszen, Transplantation, vol. 23, No. 1, Feb. 1991, pp. 785–786.

P.Y. Benhamou et al., "Ultraviolet Light Irradiation Reduces Human Islet Immunogenicity Without Altering Islet Function," *Horm. Metab. Res.*, 27,113–120 (1995).

(List continued on next page.)

*Primary Examiner*—John Kim
*Attorney, Agent, or Firm*—Mueting, Raasch, Gebhardt & Schwappach, P.A.

[57] ABSTRACT

A method, a solution and a chamber for the preparation and storage of pancreatic islets. The method includes contacting a pancreas with a warm collagenase solution, digesting the pancreas in the warm collagenase solution to form warm digest, adding cold preservative solution to the warm digest, agitating the warm digest/cold preservative solution at a temperature between about 0° and 15° C., to thereby further digest the partially digested pancreas included in the warm digest, to form cold digest and collecting liquid from the cold digest to form isolated islets. The cold preservative solution and a pancreatic islet preservative solution of the present invention include D-mannitol, K-lactobionate and a buffer.

12 Claims, 1 Drawing Sheet

OTHER PUBLICATIONS

P.Y. Benhamou et al., "Human Islet Isolation in 104 Consecutive Cases," *Transplantation*, 57(12), 1804–1810 (1994).

Gray et al., "The Use of Fluorescein Diacetate and Ethidium Bromide as a Viability Stain for Isolated Islets of Langerhans," *Stain Technology*, 62(6), 373–381 (1987).

M.P.M. van der Burg et al., "Pancreatic Islet Isolation with UW Solution: A New Concept," *Transplantation Proceedings*, 22(4), 2050–2051 (1990).

Fig. 1

METHOD OF PRESERVING PANCREATIC ISLETS

This invention was made with government support under grant DK20827, awarded by The National Institutes of Health. The United States government has certain rights in this invention.

1. Field of the Invention

This invention is directed at the preparation and storage of pancreatic islets for transplantation into diabetic patients.

2. Background of the Invention

Pancreatic islet transplantation has the potential to be the most physiologically advantageous and minimally invasive procedure for treatment of type I diabetes mellitus. However, despite progressively increasing numbers of islet transplants in these patients, the endocrine function established by the transplant is far from optimum. In order for this approach to be a clinically acceptable diabetes therapy, several technical and immunological problems need to be solved.

Donor islet preparation is the first critical step to provide a sufficient number of high quality islets for transplantation. Large-scale islet preparation from the pancreas of large animal species, including dogs, pigs and humans, has become possible through the development of highly automated procedures. Islet isolation, involving the digestion of pancreatic tissue and the purification of islets, is, in particular, the most important process that influences the outcome of transplants.

Pancreatic islets are usually transplanted into diabetic patients who also need a kidney or other solid organ transplant who are already being, or will be treated with immunosuppressants in order to prevent graft rejection. Despite many attempts, to date only a small fraction of islet allografts have functioned for a prolonged period. One of the major reasons for this failure appears to be an insufficient number of islets used for transplantation. The current recommendation by the International Islet Transplant Registry is to transplant more than 6,000 islets, equivalent to 150 μm in size, per kg of the recipient's body weight in order to achieve long-term maintenance of euglycemia. To fulfill this requirement, islets from multiple donors have often been used. However, a more desirable approach would be to derive both kidney (or other organs) and islets from the same donor in order to avoid an additional antigenic load and therefore, decrease the possibility of rejection. This would require the isolation of a large number of high quality islets from a single human pancreas.

Large-scale islet isolation from the human pancreas has become possible with advances in technology and the availability of high quality collagenase used in their preparation. However, even with these improvements, the islet yield from a single pancreas is often insufficient for transplantation. It is desirable to develop a method for isolation of pancreatic islets and storage of the islets so that transplants can be prepared from a single donor.

SUMMARY OF THE INVENTION

The present invention is directed at a method, a solution and a chamber for the preparation and storing of pancreatic islets.

The method of the present invention comprises contacting a pancreas with a warm collagenase solution, digesting the pancreas in the warm collagenase solution to form warm digest, adding cold preservative solution to the warm digest, agitating the warm digest/cold preservative solution at a temperature between about 0° and 15° C., to thereby further digest the partially digested pancreas included in the warm digest, to form cold digest and collecting liquid from the cold digest to form isolated islets.

The solution of the present invention comprises a sugar derivative such as D-mannitol, K-lactobionate and a buffer.

The chamber of the present invention comprises a lower chamber for the digestion of pancreatic pieces and a lid inserted into the lower chamber. The lid comprises a cap, a filter attached to the cap, wherein the filter is placed within the lower chamber when the lid is inserted into the lower chamber, a port attached to the cap wherein digested pancreatic pieces are decanted from the lower chamber, filtered through the filter and removed from the chamber through the port and a cover attached to the port to prevent contamination of the contents of the chamber.

BRIEF DESCRIPTION OF THE FIGURE

Features, aspects and advantages of the invention will be more fully understood when considered with respect to the following detailed description, appended claims and accompanying drawing where:

DETAILED DESCRIPTION

The present invention is directed at a new isolation technique which uses an intermittent two-step digestion procedure for pancreatic tissue and includes warm and cold digestion steps. The invention is also directed at a chamber for use in the digestion procedure and a cold storage solution for storage of isolated islets and digested pancreatic tissues. The present invention has lead to the consistent isolation of a significantly higher number of islets than were achieved by previously used methods.

For the isolation of pancreatic islets in accordance with the present invention tissue is digested by a two-step procedure, first by warm digestion, then by cold digestion, as described below.

The pancreas is transported, under refrigeration or on ice, in a solution such as 30 mM raffinose, 100 mM K-lactobionate, 15 mM $KH_2PO_4$, 5 mM $MgSO_4$, 5 mM adenosine, 3 mM glutathione, 1 mM allopurinol, 8 mM dexamthazone and 5% (w/v) hydroxyethyl starch (HES), pH 7.4 or other suitable transportation medium. The organ is preferably trimmed of surrounding membranes, vessels, fat and lymph nodes to reduce the amount of "contaminating" tissue and material from the pancreas, cannulated with an angiocatheter and weighed. In a preferred embodiment of the present invention, the organ is expanded by injecting 150–250 ml of warm collagenase solution using a 30 ml syringe and sectioned into approximately 8–10 pieces. In another embodiment of the present invention the pancreas is soaked in or otherwise contacted with the collagenase solution. It will also be realized by those skilled in the art that the pancreas could be processed whole rather than being cut into pieces. In a preferred embodiment the collagenase solution includes a collagenase such as Collagenase P (Boehringer Mannheim Colo., Indianapolis, Ind.), about 2% (v/v) heat-inactivated newborn bovine serum (NBS, Sigma Chemical Co., St Louis, Mo.), about 1 mg/ml calcium chloride and about 40 mg/dl DNase in a solution such as 5.6 mM glucose, 15 mM $KH_2PO_4$, 0.33 mM $Na_2HPO_4$, 0.82 mM $MgSO_4$, 5.4 mM KCl, 137 mM NaCl and 1.3 mM $CaCl_2$, pH 7.2, although one skilled in the art will appreciate that other collagenases and components of the collagenase solution could be substituted or used and still successfully digest the pancreas. The concentration of collagenase is optimized with respect to the time required to achieve digestion of the pancreas for each lot collagenase and usually ranges from 1.5 to 2.5 mg/ml.

Figure 1:
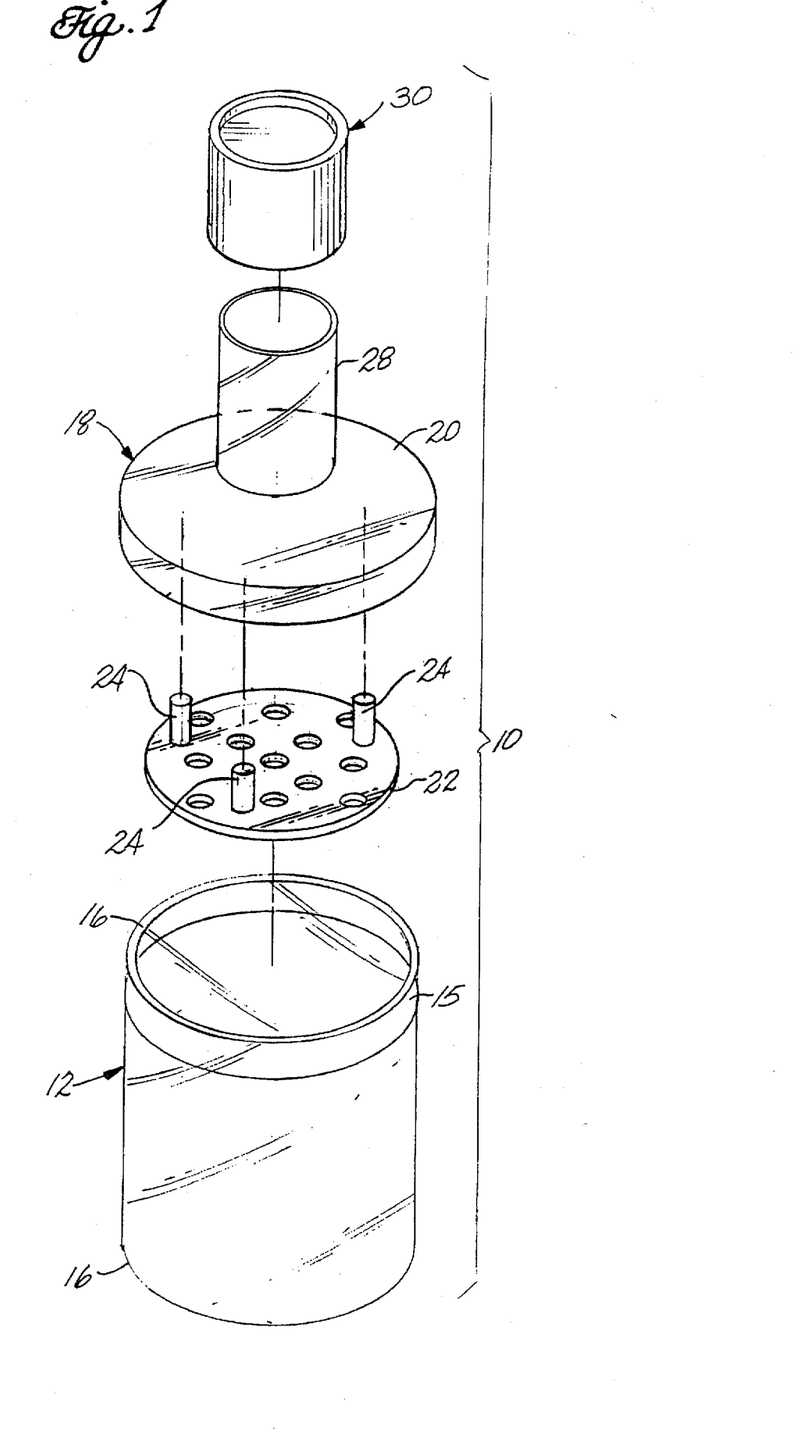
FIG. 1 is an exploded perspective view of a digestion chamber of the present invention.

In a preferred embodiment, pieces of pancreas are placed in a container, such as that described in FIG. 1, containing an agitator such as glass marbles. The chamber is gently agitated in an incubator or a water bath at about 37° C. using a shaker such as a Wrist Action Shaker Model 175 provided by Burrell Co. of Pittsburgh, Pa., for about 15 minutes, until the pancreas is partially digested (Step 1: warm digestion phase). While it is preferred that the digestion be performed at 37° C. other temperatures, at which the collagenase retains its activity, but do not result in significant damage to the pancreatic islets, could be used, generally temperatures within the range of 35° to 38° C. are suitable for pancreatic digestion.

Preferably the partially digested tissues/collagenase solution, is filtered through a sheet of large-mesh (about 5 to about 10 mm) screen into a second container and placed on ice. While filtration is preferred it will be understood that other methods of separation such as gravity sedimentation or decanting would also be applicable or, alternatively, the partially digested tissues/collagenase solution could be further processed without filtration or separation of the partially digested tissues/collagenase solution. Cold (about 4° C.) preservation solution is added to the second container at a volume approximately ⅓ of the decanted volume. The preservation solution of the present invention comprises K-lactobionate, a sugar derivative such as D-mannitol and a buffer such as $KH_2PO_4$. The preservation solution may also include a membrane stabilizer such as $MgSO_4$, a radical scavenger such as superoxide dismutase, catalase, and vitamins such as vitamin C, vitamin E and nicotinamide and combinations thereof. The concentrations of the components of the preservation solution are preferably in the range of 25 to 50 mM for D-mannitol, 80 to 120 mM for K-lactobionate, 15 mM for $KH_2PO_4$ and when used, 1 to 5 mM $MgSO_4$, superoxide dismutase at a concentration where free radicals are eliminated from the solution but not at a concentration which is so high as to be wasteful of the material and 1 to 10 mM for nicotinamide (LAP-1). In a preferred embodiment of the present invention the preservative solution comprises 30 mM D-mannitol, 100 mM K-lactobionate, 15 mM $KH_2PO_4$ and when used, 5 mM $MgSO_4$, 30,000 units/l superoxide dismutase and 5 mM nicotinamide (LAP-1).

When the method employed uses a separation step as described above, warm collagenase solution is again added to cover the remaining undigested tissue and warm digestion is repeated. After about 5 minutes, all collagenase/digested tissues in the first container are transferred into the second container. The second container is gently shaken, for example by hand, at about 4° C. or on ice. About every 5 minutes, ⅓ of the supernatant containing digested tissues is decanted, from the second container, into a collection bottle containing a cold preservative solution as described above and preferably LAP-1 solution supplemented with about 20% (v/v) serum such as newborn bovine serum. A preservative solution is added to the second container at about a volume equal to that decanted and the container is shaken again. This "cold digestion" process is repeated until all islets are freed (Step 2: cold digestion phase). If necessary, warm digestion is repeated a third time, so that only undigested, larger ductal structures remained.

To avoid harmful effects on digested tissues, collagenase and other enzymes released from pancreatic acinar cells are inactivated as soon as possible after the cold digestion step. For this purpose, digested pancreatic tissues containing free islets are collected from the second container at 5–10 minute intervals and stored on ice in a large amount of cold preservation solution which includes a high concentration of serum, although other methods of inactivating the enzymes are known to those skilled in the art. Pancreatic digests are stored in a preservation solution as described above and preferably cold LAP-1 solution supplemented with about 20% (v/v) NBS or other suitable serum.

In a preferred embodiment of the present invention, pancreatic digests are suspended in a solution such as Euro-Ficoll solution such as that supplied by Pharmacia with a density of 1.100 g/cm³ and islets are separated from acinar cells by discontinuous gradient centrifugation on three layers of Euro-Ficoll solutions (densities of: 1.100, 1.087 and 1.056) using a COBE2991 cell processor such as that supplied by Cobe Laboratories, Inc. of Lakewood, Colo. After about 10 minutes centrifugation, islet fractions are identified and collected. Islets are washed twice with a cold preservative solution such as LAP-1 and once with a medium such as RPMI1640 medium, supplied by GIBCO, containing 10% (v/v) fetal bovine serum (FBS) at room temperature. Other suitable methods of cell purification are known to those skilled in the art and would also be suitable for use in the present invention. The practice of the present invention typically provides islets with a purity of at least 70%, islets retain at least 90% of their viability and retain their ability to respond to glucose stimulus.

In a second aspect of the present invention a solution for the storage and preservation of pancreatic islets has been developed. The solution has been designated LAP-1 and comprises K-lactobionate, a sugar derivative such as D-mannitol and a buffer such as $KH_2PO_4$. The preservation solution may also include a membrane stabilizer such as $MgSO_4$, a radical scavenger such as superoxide dismutase, catalase, vitamin C or vitamin E and nicotinamide. The concentrations of the components of the preservation solution are preferably in the range of 25 to 50 mM for D-mannitol, 80 to 120 mM for K-lactobionate, 15 mM for $KH_2PO_4$ and when used, 1 to 5 mM $MgSO_4$, superoxide dismutase at a concentration where free radicals are eliminated from the solution but not at a concentration which is so high as to be wasteful of the material and 1 to 10 mM for nicotinamide. In a preferred embodiment of the present invention the preservative solution comprises 30 mM D-mannitol, 100 mM K-lactobionate, 15 mM $KH_2PO_4$ and when used, 5 mM $MgSO_4$, 30,000 units/l superoxide dismutase and 5 mM nicotinamide. Additionally, the solution may include trypsin inhibitors and other components as desired. The pH of the solution is adjusted to about 7.3 at room temperature. Newborn calf serum, or other suitable serum, is added to a concentration of about 5 to 20% (v/v) and preferably 20% (v/v) to store digested tissues. In a preferred embodiment LAP-1 comprises 30 mM D-mannitol, 100 mM K-lactobionate, 15 mM $KH_2PO_4$, 5 mM $MgSO_4$, 30,000 units/l superoxide dismutase and 5 mM nicotinamide.

The present invention is also directed at a chamber for performing warm digestion of pancreas (see FIG. 1). The chamber 10 is manufactured from a transparent material such as plastic or glass. It is preferable that the material is sterilizable by autoclaving or other suitable sterilization procedures well known to those skilled in the art. The chamber 10 comprises a lower chamber 12, which in a preferred embodiment of the present invention, is a cylinder which is closed at a first end 14 and open at a second end 16. In use pancreas pieces are added to the lower chamber along with collagenase solution described above.

In one embodiment of the present invention a lid 18 fits into and seals the second end of the lower chamber. The lid may also attach to the lower chamber by a screw fit, well known to those skilled in the art. Lid 18 comprises a cap 20 to seal the lower chamber and to prevent the contents of the lower chamber from being contaminated. In a preferred embodiment the cap is dimensioned to fit within a channel 15 positioned around the interior circumference of the lower chamber, adjacent to the second end. Cap 20, when inserted into the lower chamber fits into the channel and is held in place at the second end of the lower chamber.

Attached to the underside, the side which is inserted into the lower chamber, is a filter 22. The filter is attached to and spaced from the cap by posts 24. The filter is dimensioned to fit closely to the interior wall of the lower chamber, adjacent to channel 15, when the lid is placed on the lower chamber.

The filter includes perforations 26 to allow digested material to pass from the lower chamber, through the filter and out port 28. In a preferred embodiment of the present invention the perforations are about 0.8 mm in diameter and allow smaller digested material to be decanted from the lower chamber. Port 28 is provided with a cover 30 which is dimensioned to slidably mate with the exterior of port 28 to seal the port to prevent contamination of the interior of the chamber. The cover may also attach to the port by a screw fit, well known to those skilled in the art.

EXAMPLE 1

Isolation of Pancreatic Islets and Comparison of Storage Solutions

Ten consecutively harvested human pancreas (7 male and 3 female) were used in this study. All pancreata were harvested, after obtaining appropriate consent, from cadaveric organ donors and transported in cold solution of 30 mM raffinose, 100 mM K-lactobionate, 15 mM $KH_2PO_4$, 5 mM $MgSO_4$, 5 mM adenosine, 3 mM glutathione, 1 mM allopurinol, 8 mM dexamthazone and 5% (w/v) hydroxyethyl starch (HES), pH 7.4 (UW solution). The age of donors ranged from 17 to 63 years (40.8±4.7 years) and cold ischemic time ranged from 3 to 11 hours (8.4±1.0 hours).

After intraductal injection of 150–250 ml of a solution of 5.6 mM glucose, 15 mM $KH_2PO_4$, 0.33 mM $Na_2HPO_4$, 0.82 mM $MgSO_4$, 5.4 mM KCl, 137 mM NaCl and 1.3 mM $CaCl_2$, pH 7.2 (HBSS) containing 2.5 mg/ml collagenase (Collagenase P, lot #13494022-50, Boehringer Mannheim Co., Indianapolis Ind.) at 37° C., the pancreata was cut into approximately 8–10 pieces (2–3 $cm^3$) and placed in a disposable clear plastic container (500 ml in size), such as that shown in FIG. 1, with three glass marbles (1 cm in diameter). First, the pancreata was gently agitated with a shaker (Wrist Action Shaker Model 175, Burrell Co. Pittsburgh, Pa.) in a 37° C. water bath for 15–20 minutes (Step 1).

The collagenase solution containing the digested tissue was filtered through a 8 mm screen and transferred to a second clear plastic container to which ⅓ of the total amount of cold preservation solution, 30 mM D-mannitol, 100 mM K-lactobionate, 15 mM $KH_2PO_4$, 5 mM $MgSO_4$, 30,000 units/l superoxide dismutase, 5 mM nicotinamide, pH 7.3 (LAP-1) was added. This container was then hand-shaken on ice to further digest the tissues. Every 5 minutes, shaking was stopped, ⅓ of the solution containing digested tissues was removed though a 800 μm screen, the same volume of fresh cold LAP-1 solution was added to the container and the digestion continued (Step 2).

This process was repeated several times until most of the islets were freed from the tissue. The undigested tissue that remained on the 8 mm screen was further digested in a 37° C. water bath for an additional 5–10 minutes until most of the remaining tissue consisted of pancreatic ducts. Usually, this second warm digestion was sufficient to release the remaining acinar and endocrine components from the larger ductal structures. This digested tissue was also transferred into the cold digestion container, for further cold digestion. The entire procedure was completed within 60 minutes.

The following four solutions were used to store digested pancreatic tissue in the cold: HBSS, UW solution, modified UW solution which consisted of the same components as UW solution, but omitting HES, and LAP-1 solution. The components of these solutions are compared in Table I.

TABLE I

| SOLUTION | HBSS | mUW | UW | LAP-1 |
|---|---|---|---|---|
| COMPONENTS | | | | |
| Impermiants | 5.6 mM glucose | 30 mM raffinose | 30 mM raffinose | 30 mM D-mannitol |
| | | 100 mM K-lactobionate | 100 mM K-lactobionate | 100 mM K-lactobionate |
| $H^+$ buffers | 15 mM $KH_2PO_4$ | 15 mM $KH_2PO_4$ | 15 mM $KH_2PO_4$ | 15 mM $KH_2PO_4$ |
| | 0.33 mM $Na_2HPO_4$ | | | |
| Metabolites and others | 0.82 mM $MgSO_4$ | 5 mM $MgSO_4$ | 5 mM $MgSO_4$ | 5 mM $MgSO_4$ |
| | 5.4 mM KCl | | 5 mM adenosine | 30,000 U/l SOD |
| | 137 mM NaCl | | 3 mM glutathione | 5 mM nicotinamide |
| | 1.3 mM $CaCl_2$ | | 1 mM allopurinol | |
| | | 8 mM dexamthazone | 8 mM dexamthazone HES (5% w/v) | |
| $Na^+$ (mEq)[1] | 138 | 30 | 30 | 30 |
| $K^+$ (mEq) | 5.8 | 120 | 120 | 120 |
| mOsm/l[2] | 284 | 320 | 320 | 320 |
| pH | 7.2 | 7.4 | 7.4 | 7.3 |

[1] mEq = milliequivalents
[2] mOsm/l = milliosmolar/l

LAP-1 (100 mM K-lactobionate, 30 mM D-mannitol, 15 mM $KH_2PO_4$, 5 mM $MgSO_4$, 30,000 U/l superoxide dismutase-SOD from bovine erythrocytes, Sigma Chemical Co., St. Louis, Mo. and 5 mM nicotinamide-Sigma Chemical Co., St. Louis, Mo.) was adjusted to a pH of 7.3 at room temperature. Newborn calf serum was added to each solution at 20% (v/v) concentration to store digested tissues.

Four separate 50 ml plastic tubes (Fischer Scientific, Pittsburgh, Pa.), each containing 25 ml of either HBSS, UW, mUW, or LAP-1 were placed on ice. Each time tissue was removed from the container during the cold digestion process, the tissue was dispensed equally between the four tubes until an equal amount of digested tissue (a total of 1.5 to 2 ml) was placed in each tube. The tubes were then stored for 90 minutes on ice. The remaining digested tissues were processed by a bulk islet isolation procedure, as described below.

After 90 minutes preservation at 4° C., digested tissue from each tube was separately suspended in Euro-Ficoll solution (density of 1.100 g/cm$^3$) and purified by a discontinuous gradient centrifugation on Euro-Ficoll solutions (d=1.100, 1.087, 1.056) in HBSS at 450 x g for 20 minutes at 4° C. After centrifugation, cells were taken from each density interface to identify the islet layer. Cells in the second layer, the interface between 1.087 and 1.056 and the third layer, the interface between 1.100 and 1.087, contained islets. The islets, from the interfaces were collected and washed twice with the corresponding cold solution at 4° C., followed by one wash with RPMI1640 culture medium (see below) at room temperature. Yield and purity of islet preparations were evaluated by dithizone (DTH) staining. The islet number was expressed as 150 μm islet equivalents (IEQ).

Islets resuspended in RPMI1640 culture medium were distributed equally into six plastic Petri dishes (Falcon #1008, Becton Dickinson Co., Franklin Lakes, N.J.) per group to be used for counting the islet numbers on days 0, 1 and 3 following preparation. Additionally, three dishes of each group were prepared for evaluation of islet viability and for assessment of glucose stimulated insulin release in a static incubation assay and a perfusion system and the measurement of islet insulin content. The medium used for culture was RPMI1640 supplemented with 10% (v/v) fetal bovine serum (FBS), 10 mM nicotinamide, 25 mM HEPES, 24 mM NaHCO$_3$, 100 units/ml penicillin G, 100 μg/ml streptomycin and 0.25 μg/ml amphotericin B. All culture dishes were placed in a tissue culture incubator in a 5% (v/v) CO$_2$/air environment, at 37° C.

Islet Yield

Immediately after isolation, the total islet yield in each group was evaluated, in duplicate, using DTH staining. The islet number was converted to 150 μm islet equivalents (IEQ). The result of each group was expressed as a percentage of the islet number yielded with HBSS in each series.

Islet Purity After Isolation

The sample used for counting islet yield was also used to evaluate the purity of islet preparations. The purity was estimated from the proportion of DTH stained and unstained cells. The result was expressed as a percentage of the DTH stained cell number to the total cell number.

Islet Numbers During Culture

Islet numbers in two randomly selected dishes were counted on days 0, 1 and 3 (day 0 is the day of islet isolation) using DTH staining.

Viability of the Islets

On days 0, 1 and 3 of culture, the viability of islets was assessed using supravital staining with fluorescein diacetate and ethidium bromide as described by Gray et al., *Stain Technology* 62 373-381 (1987). The viability of each islet was scored as 0 (0%: dead islet), 1 (25% viable islets), 2 (50% viable islets), 3 (75% viable islets) and 4 (100%: fully viable islet) and the percent viability was calculated from the following formula:

% viability=(0.25×number of islets scored as 1+0.5× number of islets scored as 2+0.75×number of islets scored as 3+number of islets scored as 4) divided by total islet number×100.

Insulin Release Assay

To assess β-cell function, static incubation tests were performed on each group between day 3 and day 8. One thousand islets (IEQ) were incubated in 1 ml RPMI1640 containing 60 mg/dl glucose (basal medium) for 45 minutes and then in 1 ml RPMI1640 containing 300 mg/dl glucose (high glucose stimulation medium) for 45 minutes. The islets were again incubated in 1 ml basal medium for 45 minutes. Insulin levels released into each medium were measured by solid-phase radioimmunoassay (Autopak insulin kit, ICN Biomedicals Inc., Costa Mesa, Calif.). A stimulation index was calculated as the insulin released into the stimulation medium divided by insulin released into the basal medium. After the static incubation test, insulin was extracted from the islets by overnight incubation in acid alcohol to measure islet insulin content.

In addition, dynamic insulin release in response to glucose stimulation was evaluated by a perfusion system with the islets isolated using LAP-1 cold preservation solution. Five hundred islets, placed in a cytodex gel (Cytodex 2, Pharmacia Inc, Piscataway, N.J.) column, were first perfused at 37° C. with Krebs buffer solution containing 60 mg/dl glucose and 2% (v/v) heat-inactivated newborn bovine serum for 100 minutes to stabilize the baseline. During the next 15 minutes, samples were collected every one minutes (basal insulin release). The medium was then changed to Krebs buffer containing 300 mg/dl glucose and perfused for 30 minutes before changing to the basal buffer to observe prompt shut-off of insulin release. Insulin levels in each sample collected during the perfusion (1 minute/tube) were measured by solid phase radioimmunoassay.

Electron Microscopy of Islets

Immediately after isolation, islets were fixed with 1.25% (w/v) glutaraldehyde in 0.1M phosphate buffer, pH 7.4, at room temperature for the ultrathin sectioning method. Islets were washed in 0.1M phosphate buffer containing 5% (w/v) sucrose (pH 7.4, 360 mOsm) and suspended in 70% (v/v) calf serum in 0.1M phosphate buffer, pH 7.4. Subsequently, cells were centrifuged at 450 g for 15 minutes to form a pellet which was immersed in 2% (w/v) glutaraldehyde in 0.1M phosphate buffer (pH 7.4, 440 mOsm) for 2 hours. Each pellet was cut into small blocks and washed with 0.1M phosphate buffer containing 8% (w/v) sucrose (pH 7.4, 440 mOsm) followed by post-fixation in 1% (w/v) osmium tetroxide in 0.1M phosphate buffer containing 7% (w/v) sucrose (pH 7.4, 440 mOsm) for 2 hours. The fixed specimens were dehydrated in a graded series of ethanol and embedded in epoxy resin. The thin sections were stained with uranyl acetate and lead citrate. Observations were performed with a Hitachi H-7000 transmission electron microscope.

Data Analyses

All data were expressed as mean±standard error unless otherwise specified. Differences between groups were compared using an unpaired, two-tailed Student's t-test and were considered statistically significant if p value <0.05.

Results

Immediately after islet isolation, groups mUW, UW and LAP-1 yielded higher numbers of islets than the HBSS group. The difference was statistically significant in groups mUW and LAP-1. There was a wide range of islet yields from one set of experiments to another, depending on the volume of digested tissue used. For this reason, islet yields were expressed as percent of the value obtained with HBSS. Islet yields in group LAP-1, in particular, were twice as high as those in the HBSS group (192±92%), see Table II.

Islets isolated in LAP-1 released insulin immediately after glucose stimulation with a two phase insulin release, which promptly ceased when the high glucose buffer was replaced by the basal buffer. The curve demonstrated the normal function of β-cells.

The two-step digestion technique for the human pancreata has been used successfully to isolate a large number of

TABLE II

| Sample | Raw data expressed as Islet Equivalents (IEQ) | | | | Data expresses as a percentage of the HBSS values | | | |
|---|---|---|---|---|---|---|---|---|
| | HBSS | mUW | UW | LAP | HBSS | mUW | UW | LAP |
| Hu148 | 2675 | 8267 | 2492 | 6750 | 100 | 309.05 | 93.17 | 262.34 |
| Hu153 | 14775 | 17883 | 16168 | 18467 | 100 | 121.04 | 109.36 | 124.99 |
| Hu154 | 17608 | 31641 | 18667 | 19825 | 100 | 180.72 | 106.62 | 113.23 |
| Hu166 | 31592 | 22017 | 46625 | 40160 | 100 | 69.69 | 147.68 | 127.09 |
| Hu167 | 41808 | 69475 | 38450 | 46367 | 100 | 142.26 | 91.97 | 110.9 |
| HU169 | 13442 | 19292 | 11392 | 22625 | 100 | 143.62 | 84.75 | 168.32 |
| Hu164 | 4050 | 8533 | 13167 | 14000 | 100 | 210.69 | 325.11 | 346.68 |
| Hu165 | 4930 | 8160 | 7310 | 12910 | 100 | 165.62 | 148.28 | 261.87 |
| Hu167-1 | 13687 | 22313 | 25533 | 42900 | 100 | 163.02 | 186.66 | 313.44 |
| Hu167-2 | 19380 | 21573 | 23307 | 20673 | 100 | 111.32 | 120.26 | 106.67 |
| Mean | 16385 | 21916 | 20310 | 24467 | 100 | 161.68 | 141.36 | 192.46 |
| SD[1] | 12372 | 15214 | 13723 | 13734 | 0 | 64.87 | 71.91 | 92.02 |

[1]SD = standard deviation

The purity of islet preparations in the HBSS group was 1.5±14.8%. In contrast, the purity in groups mUW, UW and LAP-1 was 71.5±8.9%, 74.9±10.7%, 75.8±7.4%, respectively, which were significantly higher than that of the HBSS group ($p<0.001$). Differences between these three groups, however, were not significant. Highly purified islets (as high as 95% pure) were isolated with LAP-1. In contrast, islets in the HBSS group were contaminated with exocrine tissue and the purity was as low as 25%.

In the HBSS group, the islet numbers decreased to 55.6±14.4% on day 1 and 27.4±16.5% on day 3 as compared to that on day 0 (100%). In contrast, significantly higher numbers of islets were counted in all other groups on both days 1 and 3 as compared to those in the HBSS group. Especially in group LAP-1, the islet number was maintained at the highest level of 94.6±20.4% on day 1 and 78.5±24.2% on day 3, but a significant difference was not obtained between groups mUW and UW.

At the time of islet isolation, the percent viability estimated by staining with fluorescein diacetate and ethidium bromide was already lowest in the HBSS group (HBSS vs UW, HBSS vs LAP-1; $p<0.05$). Islet viability in this group continuously decreased to 37.4±19.5% on day 1 and 16.8±13.2% on day 3, whereas the other three groups maintained significantly higher islet viability. As shown by a electromicrograph of a representative case, islet damage was clearly less in the LAP-1 group than that in HBSS.

Contamination with cell debris and acinar cells was more prominent in the HBSS group as compared to LAP-1. In addition, islet cells in the HBSS group displayed a decreased density of cytoplasm, mitochondrial swelling and unclear or ruptured cell membranes. By contrast, these findings were consistently less frequent in the LAP-1 group.

The highest insulin content was found in islets isolated with LAP-1. However, no statistically significant differences were detected between any of the groups.

In groups mUW, UW and LAP-1, the stimulation indices were higher than that of the HBSS group. In particular, in groups mUW and LAP, the indices were significantly higher than that of the HBSS group.

viable islets. The technique involves two phases of digestion processes, first at 37° C. and then on ice. In cold digestion, the collagenase solution was gradually replaced by cold preservation solution. The tissue is broken down into smaller fragments by warm collagenase digestion, it continues to digest on ice into fine fragments and finally to free islets. Islets prepared by the two-step procedure maintained a well preserved capsule and an excellent three-dimensional structure. This method prevents overexposure of islets to collagenase and thus avoids over-digestion of islets as well as acinar cells.

UW solution is the most advanced and widely used cold preservation solution for storing organs awaiting transplantation. UW solution contains a low concentration of $Na^+$ and high concentration of $K^+$, similar to the composition of intracellular fluid. In addition, UW solution contains the lactobionate anion and raffinose as impermeable components and HES to maintain the colloid pressure. This composition prevents cell swelling that occurs when cells are stored in conventional physiological solutions (i.e. HBSS) in the cold, a condition in which the cell membrane sodium-potassium pump ceases to function. Although HES is an important component for maintaining vascular networks when an organ is flushed out with cold preservation solution, it may be omitted, with no deleterious effect on cell viability, in cold storage of small organs or tissues. We therefore modified the UW solution to contain only lactobionate-$K^+$, raffinose, $KH_2PO_4$ and $MgSO_4$ and compared the effectiveness of both mUW and UW in this study. Along with these tests, we also developed a new cold preservation solution, LAP-1, for islets with special attention to their vulnerability. LAP-1 solution contains lactobionate and D-mannitol as impermiants, to inhibit cell swelling by maintaining extracellular osmotic pressure. D-mannitol is also known to have a scavenging activity for hydroxy radicals (OH•) to which β-cells are highly susceptible. As with UW solution, LAP-1 solution contains $KH_2PO_4$ as a component of the buffering system. In addition, the solution contains SOD (30,000 units/l) and nicotinamide (5 mM/l). Our expectation is that SOD and nicotinamide would enter islet cells, that may have been damaged during the isolation process, to protect them from further damage and to support their recovery in culture or after being transplanted.

In this study, the performance of four solutions for storing digested pancreatic tissue at low temperature have been compared by evaluating the yield, the purity of the recovered islets and the viability of islets maintained in culture. Cell viability was also assessed by electron microscopic examination of islets and by β-cell function. The yield and purity of isolated islets were markedly improved by using solutions especially designed for cold storage of organs (UW, mUW, LAP-1), instead of using cold HBSS. Although HBSS has been widely used for human islet isolation, the first interface between HBSS and 1.056 g/cm$^3$ Euro-Ficoll contained many fragmented islets and the second interface between 1.056 and 1.088 g/cm$^3$ Euro-Ficoll contained most islets and a considerable number of exocrine cells. This indicated that the density of both islet and acinar cells had changed significantly, probably due to cell swelling during cold storage. This resulted in more islet destruction (thus, lower yield) and lower islet purity. In contrast, with other solutions, almost all islets were found in the second interface with far fewer acinar cells, indicating that UW, mUW and LAP-1 solutions prevented cell swelling and had maintained the density of both islet and exocrine tissues. Electron microscopic examination of islets isolated with LAP-1 solution revealed no cell swelling and a normal structure of islet cells. Since the islet yield and purity were not significantly different between these three solutions, HES and raffinose may not be essential components of the cold preservation solution for preventing cell swelling under the conditions used in the islet isolation.

Islet numbers were also counted during culture for three days. The islet number on day 1 was especially important, since it probably reflects an actual islet number that may survive following transplantation. On day 1, the islet numbers in the HBSS group had already decreased by nearly 50% and declined to only 25% of the initial count on day 3. This decline indicated severe and often irreversible damage to islets that occurred during the cold storage of pancreatic digests. Islet numbers in the other three groups were significantly higher at all points, ranging between 95% and 75% on day 1 and between 78% and 60% on day 3, as compared to those on day 0. The decreased islet numbers and viability on day 3 in this study may have been influenced by the culture conditions, since only a small volume of culture medium was used in order to accommodate islet counting. Although no significant differences were found between these three groups, islet viability was higher in groups UW and LAP-1. These results show that the prevention of cell swelling during the islet isolation process contributes not only to the improvement of islet yield and purity, but also to greater islet viability. The results of β-cell functional tests correlated with these viability results. The stimulation index was highest in the LAP-1 group. However, islet insulin content, as expressed by μU/islet (IEQ), did not show any differences between the groups. This is not surprising, since an equal number of islets, that survived for more than 3 days in culture, was used for these tests. This also indicates that islets recover fully in culture by day 3 and survive.

The beneficial effects of UW, mUW and LAP-1 solutions over HBSS have been clearly demonstrated in the preparation of human pancreatic islets. Among these, LAP-1 solution was most effective, providing the best yield, purity and viability of isolated islets. Also, the high viscosity of the UW solution made it undesirable for use in the isolation of islets as manipulations with the viscous solution were difficult. In a perfusion system to test dynamic insulin release in response to high glucose stimulation, islets in the LAP-1 group exhibited excellent functional responsiveness.

Pancreatic islets have two different characteristics: one as a cell and another as an organ. The islet acts as a miniature organ, since it consists of several different cell types which interact functionally with one another and has its own vascular system. In order to maintain normal islet function, islet structure needs to be preserved carefully. The collagenase digestion process is a procurement process of islets from the larger organ, the pancreata, under warm ischemic conditions. The subsequent processes, that include cold storage, purification and washing of islets, correspond to the cold anaerobic preservation of a donor organ. Based on the well documented theory for organ harvesting, shortening of the warm ischemic process is the first critical issue and the use of an appropriate preservation solution for cold storage is the second critical issue in the procurement of highly viable donor organs. The intermittent two-step digestion procedure to minimize warm anaerobic ischemia and the use of LAP-1 solution for cold preservation of digested pancreatic tissue, both follow this basic theory. Their use resulted in higher yield, purity and viability of islets from the human pancreata.

Human islets were isolated by an intermittent two-step collagenase digestion procedure with warm collagenase digestion of the pancreata in less than 20 minutes. The cold digestion process and the cold storage of digested tissue (containing islets) should use an appropriate cold preservation solution. LAP-1 was designed as a cold preservation solution especially for islets; it showed clear advantages in the preparation of high quality islets and is also economical for use in a large quantity.

EXAMPLE 2

Preparation of Donor Pancreas

A total of 46 human pancreata were processed consecutively for islets using the new isolation procedures, described above in Example 1 (group 1). Islet preparations from 46 pancreata processed by a conventional isolation procedure served as the control group (group 2).

All pancreata were harvested with appropriate consent from cadaveric organ donors through the two organ procurement agencies of Southern California. Procurement was performed by the standard techniques, by either the members of the UCLA Liver Transplant Program or surgeons from other institutions. All organs used in this study were a part of the pancreas containing the body and tail. The mean donor age of group 1 was 33±3.2 years and ranged from 5 to 64 years; in group 2, the mean age was 36±2.7 years, ranging from 11 to 69 years and there were no significant differences between two groups. The pancreata was transported to the laboratory in either UW solution or Euro-Collins solution. Cold ischemic time in groups 1 and 2 was 8.1±0.4 hours and 6.6±0.5 hours, respectively, and not significantly different. The organ was trimmed of surrounding membranes, vessels, fat and lymph nodes, cannulated with an angiocatheter and weighed. The organ was expanded by injecting 150–250 ml of warm collagenase solution using a 30 ml syringe and sectioned into approximately 8–10 pieces. The collagenase solution contained Collagenase P (Boehringer Mannheim Colo., Indianapolis, Ind.), 2% (v/v) heat-inactivated newborn bovine serum (NBS, Sigma Chemical Co., St Louis, Mo.), 1 mg/ml calcium chloride and DNase in HBSS. The concentration of collagenase was optimized for each lot and ranged from 1.5 to 2.5 mg/ml.

For group 2, pancreatic tissues were enzymatically digested by a one-step procedure in a 37° C. water bath. The procedure has been described in detail by Benhamou et al., *Transplantation* 57 1804–1810 (1994). Briefly, the sectioned pancreas was placed in a 5×7 cm stainless-steel, enclosed mesh container containing three 1.5 cm glass marbles. The container was then placed into a disposable clear plastic chamber and the tissue was covered by collagenase solution. The total collagenase volume, used both for expansion of the organ and solution placed in the container, was approximately 200 ml. The chamber was agitated in a 37° C. water bath via a swing-arm shaker (Wrist Action Shaker, Model 75, Burrell Co., Pittsburgh, Pa.). Samples were taken at regular intervals. When free islets were noted, usually within 15 minutes after the start of digestion, the collagenase and digested tissue mixture were removed from the chamber. Sufficient fresh warm collagenase solution was added to the chamber to cover the remaining tissues and the digestion was continued. This process was repeated every 5 minutes until no more free islets were detectable, or until all tissues were digested. The total process required 45 to 60 minutes and the total collagenase solution was up to 600 ml. The collagenase/digested tissue mixture decanted from the container was immediately diluted with cold HBSS containing 20% (v/v) NBS and stored on ice until digestion was completed.

For group 1, tissues were digested by a two-step procedure, first in a 37° C. water bath, then followed by cold digestion of the partially digested tissues on ice. Pieces of the pancreas were placed in a disposable, clear plastic container containing three glass marbles. The chamber was gently agitated in a 37° C. water bath via a swing-arm shaker as above, for 15 minutes, until the pancreas was partially digested (Step 1: warm digestion phase). Collagenase solution containing partially digested tissues was filtered through a sheet of large-mesh (8 mm) screen into a second clear plastic container placed on ice. Cold LAP-1 preservation solution was added to the second container at a volume approximately ⅓ of the decanted volume. In the first container, warm collagenase was again added to cover the remaining tissue and warm digestion was repeated. After 5 minutes, all collagenase/digested tissues in the first container were transferred into the second container. The second container was connected to a collection bottle and the cold preservation solution via two separate side ports. The second container was gently hand-shaken on ice. Every 5 minutes, ⅓ of the supernatant containing digested tissues was decanted, through an out-flow port, into a collection bottle containing cold LAP-1 solution supplemented with 20% (v/v) NBS. LAP-1 solution was added to the second container, via another port, at a volume equal to that decanted and the container was shaken again. This cold digestion process was repeated until all islets were freed (Step 2: cold digestion phase). If necessary, warm digestion was repeated a third time, so that only undigested, larger ductal structures remained.

To avoid harmful effects on digested tissues, collagenase and other enzymes released from pancreatic acinar cells must be inactivated as soon as possible. For this purpose, finely digested pancreatic tissues containing free islets were collected at 5–10 minute intervals and stored on ice in a large amount of cold storage solution. In group 1, pancreatic digests were stored in cold LAP-1 solution supplemented with 20% (v/v) NBS, whereas in group 2, tissues were stored in cold HBSS containing 20% (v/v) NBS.

Pancreatic digests in both groups were suspended in Euro-Ficoll solution with a density of 1.100 g/cm$^3$ and islets were separated from acinar cells by discontinuous gradient centrifugation on three layers of Euro-Ficoll solutions (densities of: 1.100, 1.087 and 1.056) using a COBE2991 cell processor (Cobe Laboratories, Inc., Lakewood, Colo.). After 10 minutes centrifugation, islet fractions were identified and collected. Islets were washed twice with cold LAP-1 solution and once with RPMI1640 medium containing 10% (v/v) fetal bovine serum (FBS) at room temperature.

Isolated islets were cultured in plastic Petri dishes (Falcon #1005, Becton Dickinson Co., Franklin Lakes, N.J.) at 37° C. with RPMI1640 containing 20% (v/v) FBS, 10 mM nicotinamide, 25 mM HEPES, 24 mM NaHCO$_3$, 100 units/ml penicillin G, 100 mg/ml streptomycin and 0.25 mg/ml amphotericin B.

Temperature

The temperature of the digestive medium during the cold digestion phase in the intermittent two step digestion process (group 1) was monitored every 5 minutes in five isolation cases.

Islet Yield

Immediately after isolation, the total islet yield was evaluated in duplicate by taking a known volume of sample and staining with dithizone (DTH). The islet number was counted, each size separately and the total islet number converted to that equivalent to islets 150 µm in size (IEQ). The islet yield was expressed as the total islet number isolated from a given pancreas and the number of islets per gram of pancreatic tissue.

Islet Purity

The purity of the islet preparation was evaluated on the same sample as that used for islet counting and was calculated as the ratio between DTH-stained and total cells, expressed as a percentage.

Assessment of Viable Islets After 48 Hours in Culture

Islets that remained viable in culture for 2 days were taken as "viable" islets that would survive, in vivo, after transplantation. This was evaluated by placing islets in culture and assessing their viability 48 hours after isolation. Islet viability was determined using DTH for counting and fluorescein diacetate and ethidium bromide (FDEB) staining for viability assessment as described by Gray et al., *Stain Technology* 62 373–381 (1987).

In Vitro Insulin Release Assays

To assess the α-cell function of cultured islets, two glucose stimulation tests, static incubation and a dynamic insulin release assay in a perfusion system, were performed on several randomly selected preparations in group 1.

i) Static incubation assay:

One thousand islets (IEQ) were incubated successively in basal, stimulation and basal medium as described above. RPMI1640 medium was used with the glucose level reduced to 60 mg/dl for the basal medium and increased to 300 mg/dl for the stimulation medium. Insulin released during each incubation was measured by a solid-phase radioimmunoassay using human insulin as standard (Autopak Insulin Kit, ICN Biomedicals Inc., Costa Mesa, Calif.).

The stimulation index was calculated as: insulin released into the stimulation medium divided by insulin released into the basal medium. ii) Dynamic insulin release assay in a perfusion system: Five hundred islets (IEQ) were layered in a cytodex bead column, which was placed in a 37° C. water bath and perfused successively in the following order: basal, stimulation and basal medium as described previously by Benhamou et al. (*Hormone & Metab. Res.* 27 113–120, 1995). Media used in the perfusion system were Krebs Ringer bicarbonate buffer solutions containing 60 mg/dl (basal) and 300 mg/dl (stimulation) glucose, respectively. Insulin was assayed as for static incubation.

In Vivo Islet Function Test

The ability of islets to reverse diabetes was assessed, in vivo, by transplanting them into athymic mice made diabetic with an intravenous injection of 165 mg/kg streptozotocin. Islets (1,000–1,200 IEQ) from group 1, cultured for 3 days, were transplanted under the left renal capsule of diabetic mice. After transplantation, levels of non-fasting blood glucose, urine glucose and body weight were monitored three times a week. Glucose tolerance tests were also performed on day 14 by injecting 0.5 g/kg glucose into the tail vein and a K-value was calculated using blood glucose levels at 5, 10, 30 and 60 minutes after glucose challenge. On day 20 or 21, mice underwent a left nephrectomy to confirm the recurrence of diabetes and grafts were examined histologically.

Statistical Studies

All data were expressed as mean value±standard error of the mean and the difference between groups 1 and 2 was considered significant if the p-value was less than 0.05, using a two-tailed unpaired student t-test. The significance of differences in viable islet recovery was examined using a chi-square test.

There were no significant differences between groups 1 and 2 with regard to the donor age, the cold ischemia time and harvesting conditions. The pancreas weight was also similar in both groups; 55±2.7 g in group 1 as compared to 56±3.4 in group 2.

TABLE III

| Group | $n^1$ | Pancreas Weight (g) | Digestion Time Warm | Digestion Time Cold | Total |
|---|---|---|---|---|---|
| 1 | 46 | 55 ± 2.7 | 21.5 ± 0.7 | 41.7 ± 1.2 | 59.3 ± 2.5 |
| 2 | 46 | 56 ± 3.4 | 56.1 ± 2.2 | — | 56.1 ± 2.3 |
| p-value | | $N.S.^2$ | p < 0.001 | — | N.S. |

[1] n = number of isolations
[2] N.S. = Not significant

As shown in Table III, the duration of warm digestion was significantly less in group 1 (21.5±0.7 minute) compared to that in group 2 (56.1±2.3 minute). In group 1, warm digestion was followed by cold digestion for 41.7±1.2 minute, so that the total time required to digest the pancreas was 59.3±2.5 minute, similar to that of group 2.

Temperature of the medium was measured during the cold digestion procedure (n=4) Table IV.

TABLE IV

| Time (min.) | Average Temp. (°C.) | Time (min.) | Average Temp. (°C.) |
|---|---|---|---|
| $0^1$ | 37 | 30 | 15 |
| 5 | 37 | 35 | 12 |
| 10 | 37 | 40 | 10 |
| 15 | 37 | 45 | 9 |
| $20^2$ | 30 | 50 | 7 |
| 25 | 20 | 55 | 6 |

[1] Time 0–15 min.: Warm digestion process
[2] Time 20–55 min.: Cold digestion process Also, the change in the collagenase concentration during this process was calculated based on the amount of LAP-1 solution added each time, see Table V.

TABLE V

| Time (min.) | Collagenase (mg/ml) | Time (min.) | Collagenase (mg/ml) |
|---|---|---|---|
| $0^1$ | 2.5 | 30 | 0.75 |
| 5 | 2.5 | 35 | 0.50 |
| 10 | 2.5 | 40 | 0.30 |
| 15 | 2.5 | 45 | 0.20 |
| $20^2$ | 1.6 | 50 | 0.15 |
| 25 | 1.2 | 55 | 0.10 |

[1] Time 0–15 min.: Warm digestion process
[2] Time 20–55 min.: Cold digestion process By the repeated replacement of warm collagenase solution with cold LAP-1 solution during the cold digestion process, the temperature of the solution rapidly declined from the initial 37° C. to 15° C. in less than 30 minutes, then to <10° C. by 40 minutes. By dilution calculations, the collagenase concentration also decreased from 2.5 mg/ml to 0.1 mg/ml by the end of the digestion period.

Islets were successfully isolated from 44 of the 46 pancreata in group 1 (success rate: 95.6%) and from 33 of the 46 pancreata in group 2 (71.7%; p<0.01). In 9 of the 13 failures in group 2, the isolation process was terminated before the islet purification step with the COBE2991 cell processor due to an insufficient number of islets and their poor appearance during digestion. In the remaining 4 cases, most of the islets disappeared or disintegrated after the purification process.

In group 1, the total islet yield was also significantly higher than that of group 2 as shown in Table VI.

TABLE VI

| Total Yield[1] | | Yield/g Pancreas[1] | |
|---|---|---|---|
| Group | Cells × $10^3$ | Group | Cells × $10^3$ |
| 1 ($n^2$ = 44) | 336 ± 36 | 1 (n = 44) | 6.2 ± 0.7 |
| 2 (n = 33) | 196 ± 25 | 2 (n = 33) | 3.6 ± 0.3 |

[1] Islet numbers shown by IEQ
[2] n = number of isolations

The islet yield in group 1 was 335,739±36,244 IEQ from the body and tail of the pancreas (pancreas weight: 33±3.2 g) and 6,233±681 IEQ/g of tissue, while that in group 2 was 195,587±25,242 IEQ per pancreas (pancreas weight: 36±2.7 g) and 3,763±509 IEQ/g (p<0.01). The purity of isolated islets was 83.6±2.5% in group 1 and 69.2±4.7% in group 2 (p<0.05), see Table VII.

TABLE VII

| Group | Purity |
|---|---|
| 1 ($n^1$ = 44) | 84 ± 3 |
| 2 (n = 33) | 69 ± 5 |

[1] n = number of isolations

Islets placed in culture were viable, as assessed by FDEB staining, after 48 hours in 43 of the 44 successful isolations in group 1, see Table VIII.

TABLE VIII

| Group | Viable | Non-Viable |
|---|---|---|
| 1 (n[1] = 44) | 43 (97.7%) | 1 (2.3%) |
| 2 (n = 33) | 26 (78.8%) | 7 (21.8%) |

[1]n = number of isolations

Thus, overall, 43 of a total of 46 pancreata prepared by our new procedure provided viable islets as assessed by highly strict criteria. With these criteria, the success rate in group 1 was 93.5%. In contrast, islets in group 2 were viable after 2 days in culture in 26 of the 33 successful isolations (see Table VIII). Thus, the overall success rate was 56.5% (26 of the 46) in this series of isolations. The difference between groups 1 and 2 was significant (p<0.001).

Static incubation assays were performed on six different islet preparations in group 1. Stimulation indices calculated from these experiments are shown in Table IX.

TABLE IX

| Exp. No. | Stimulation Index |
|---|---|
| Hu153 | 1.91 |
| Hu154 | 1.91 |
| Hu164 | 3.03 |
| HU166 | 1.09 |
| Hu167 | 2.65 |
| Hu168 | 1.15 |
| Mean ± SE | 1.96 ± 0.32 |

Islets in all preparations responded to high glucose stimulation, although the stimulation indices were lower in #166 and #168. As represented by preparation #196 (see Table X), dynamic perfusion studies also demonstrated normal β-cell function of islets prepared in group 1 as shown by immediate and two phase insulin release after a high glucose challenge and the prompt increase in insulin release when the medium was changed to basal.

TABLE X

| $T^1$ | $G^2$ | $IRI^3$ | $T^1$ | $G^2$ | $IRI^3$ | $T^1$ | $G^2$ | $IRI^3$ | $T^1$ | $G^2$ | $IRI^3$ |
|---|---|---|---|---|---|---|---|---|---|---|---|
| 2 | 60 | 48 | 22 | 300 | 170 | 42 | 60 | 108 | 62 | 60 | 45 |
| 4 | 60 | 50 | 24 | 300 | 164 | 44 | 60 | 100 | 64 | 60 | 65 |
| 6 | 60 | 40 | 26 | 300 | 160 | 46 | 60 | 85 | 66 | 60 | 45 |
| 8 | 60 | 55 | 28 | 300 | 155 | 48 | 60 | 70 | 68 | 60 | 50 |
| 10 | 60 | 54 | 30 | 300 | 160 | 50 | 60 | 68 | 70 | 60 | 30 |
| 12 | 60 | 45 | 32 | 300 | 164 | 52 | 60 | 68 | 72 | 60 | 28 |
| 14 | 300 | 160 | 34 | 300 | 125 | 54 | 60 | 55 | 74 | 60 | 32 |
| 16 | 300 | 145 | 36 | 300 | 130 | 56 | 60 | 52 | 76 | 60 | 30 |
| 18 | 300 | 155 | 38 | 300 | 125 | 58 | 60 | 45 | 78 | 60 | 30 |
| 20 | 300 | 165 | 40 | 300 | 110 | 60 | 60 | 52 | 80 | 60 | 30 |

[1]T = Time (minutes)
[2]G = Glucose (mg/dl)
[3]IRI = Immunoreactive insulin (μU/ml)

Reversal of diabetes in athymic mice was achieved by transplantation of 1,000–1,200 islets from group 1, see Table XI.

TABLE XI

| | $NFBG^1$ | | | $NFBG^1$ | |
|---|---|---|---|---|---|
| Day | Mouse 1 | Mouse 2 | Day | Mouse 1 | Mouse 2 |
| −5 | 100 | — | 6 | 140 | 140 |
| −3 | — | 110 | 10 | — | 60 |

TABLE XI-continued

| | $NFBG^1$ | | | $NFBG^1$ | |
|---|---|---|---|---|---|
| Day | Mouse 1 | Mouse 2 | Day | Mouse 1 | Mouse 2 |
| $0^2$ | 360 | 350 | 15 | 60 | 95 |
| 1 | — | 195 | 21 | $100^3$ | — |
| 2 | 195 | — | 22 | 280 | $120^3$ |
| 3 | — | 120 | 23 | — | 400 |
| 4 | 120 | — | 24 | 390 | — |

[1]NFBG = non-fasting blood glucose
[2]day of transplant
[3]day of nephrectomy (graft removal)

Mice became normoglycemic (<150 mg/dl) with negative urine glucose within 5 days after grafting. K-values of the IVGTT were 0.30±0.02%/minutes. Histological examination with hematoxylin-eosin staining revealed well-formed islets and well-preserved β-cells as indicated by insulin staining. These in vivo results demonstrated survival and function of islets after transplantation.

Islet transplantation has not yet become a routine procedure for diabetic kidney recipients, due to a low success rate and the relatively short period of insulin independence. Islet isolation from donor pancreas is the initial process crucial to realizing successful islet transplantation. At present, simultaneous kidney and islet transplantation for type I diabetic patients with end stage renal failure would be the most reasonable form of islet transplantation because of the need for immunosuppression. In these patients, the use of islets isolated solely from the pancreas of the kidney donor would be the best approach to minimizing rejection by avoiding additional antigenic disparities. To make this possible, a large number of islets need to be isolated from a single human pancreas. Another important issue for successful islet transplantation is the ability to obtain high quality islets which survive and function well after grafting.

There are several factors that affect islet viability during islet preparation. Donor factors, the surgical techniques for the removal of the pancreas and the preservation solution used for transporting the procured pancreas can influence islet viability and recovery. Hospitalization period of the donor also affects the isolation outcome. In the islet isolation process, the most critical procedure is that of the collagenase digestion. This process is essential for separation of islets from the surrounding tissues, but, at the same time, islets can be damaged by both warm ischemic injury and enzymatic digestion mediated by collagenase and possibly enzymes released from acinar cells. Another critical procedure is the handling of islets during the cold phase of the isolation process, which involves cold storage of pancreatic digests, the islet purification process and cell washing. If not properly processed, islets may suffer cell swelling and cold ischemic injury. Additionally, islet survival can be affected by mechanical damage induced by pipetting and cell washing.

Collagenase distention of the pancreas and the digestion of tissues are an essential process for freeing islets, but are also harmful for both islets and acinar cells. In order to minimize the toxic effect of enzymes, the following three modifications are necessary: i) to reduce warm digestion time, ii) to minimize the exposure of freed islets to warm enzyme solution and iii) to stop enzyme activities by immediately storing digested tissues and freed islets in a suitable cold preservation solution. In this study, we have demonstrated that prolonged warm collagenase digestion is not necessary in order to free islets. The exposure of pancreatic tissues to warm collagenase can be reduced to less than 25 minutes. Tissue digestion continues on ice and releases islets. With the isolation technique of the present invention, the warm digestion time was significantly reduced from 50 minutes, required by earlier methods, to approximately 20 minutes. Since most of the islets were freed during the cold digestion process, the intermittent two-step procedure minimized the direct exposure of islets to warm, concentrated enzyme solution. Moreover, during cold digestion the enzyme solution was gradually replaced by the cold preservation solution and thus, islets were released into cold, diluted enzyme solution, which was further diluted by the cold preservation solution when digested tissues were stored.

The temperature of the digestion medium was rapidly lowered to 5°–7° C. during the cold digestion phase. Also, the concentration of collagenase in the digestion medium decreased to 0.1 mg/ml based on the dilution calculations. The results indicate that free islets may disintegrate by enzyme action during the warm digestion process. It was also noted that the amount of collagenase used in the two-step digestion was less than that used in the one-step procedure (up to 300 ml vs. 500–600 ml). By combining the two-step digestion procedure and the use of LAP-1 solution as a cold preservation solution, the success rate for obtaining viable islets markedly improved to 93.5% (43 of the 46 consecutive isolations) from 56.5% (26 of 46) prepared by our old method (as assessed after 48 hours in culture). Prior to this study, these isolation failures were attributed to various conditions including the donor's physical condition, medications, procurement techniques and/or prolonged cold ischemia time. Although these factors influence the outcome of islet isolation, the results in the present study suggest that the failure of isolation, poor viability of islets and lower islet yields can also result from prolonged warm collagenase digestion and cold ischemic injury during cold preservation in HBSS. It would also appear that the new isolation technique can isolate islets from a damaged pancreas by providing conditions that avoid further islet damage and preserve viable islets, whereas islet damage may be accelerated by the conventional technique.

Both islet yield and purity were improved in group 1. After density gradient centrifugation, islets were located in a confined area of the Euro-Ficoll, separate from the acinar cells. In contrast, islets and acinar cells in group 2 were distributed in a broader range of Euro-Ficoll layers. The prevention of cell swelling also increases islet yields. All pancreata used in both groups 1 and 2 were partial, containing only the body and tail. On separate occasions, islets were isolated from the whole pancreas using the newly developed technique. In all cases greater than 500,000 IEQ were isolated. This number of islets fulfills the requirement for transplantation currently recommended for type I diabetic patients by providing >6,000 IEQ/kg of recipient body weight, >90% purity and >95% viability. The recovery of viable islets after 48 hours in culture is an important index for the prediction of islet survival following transplantation. In group 2, 20% of successfully isolated islet preparations (as assessed immediately after isolation) died after being placed in culture, suggesting that irreversible islet damage occurred during the isolation process. In contrast, islets in only one of the 44 successful isolations in group 1 were lost in culture and islets were fully viable in the remaining 43 cases. These islets responded with normal insulin release in both in vitro and in vivo assays.

Although the two-step digestion procedure appears complex, the cold digestion process can be performed in a totally enclosed system, similar to that designed for our old method. The process is economical in regard to both time and personnel. The entire procedure can be carried out by two or three trained individuals within 4 to 5 hours, from the start of cleaning of the pancreas to either placing isolated islets in culture or completing the packaging for transplantation. Thus, simultaneous islet and kidney transplantation is possible. With this technique, a sufficient number of islets to fulfill the transplantation requirement can be isolated from one pancreas and simultaneous kidney and islet transplantation is possible from a single donor.

All references cited above are hereby incorporated herein by reference in their entirety.

The above descriptions of exemplary embodiments of are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A pancreatic islet preservative solution comprising D-mannitol, at least about 80 mM K-lactobionate and a buffer.

2. A pancreatic islet preservation solution as recited in claim 1 further comprising a membrane stabilizer, a radical scavenger and nicotinamide.

3. A pancreatic islet preservative solution comprising D-mannitol, at least about 80 mM K-lactobionate and $KH_2PO_4$.

4. A pancreatic islet preservative solution as recited in claim 3 further comprising $MgSO_4$, superoxide dismutase and nicotinamide.

5. A pancreatic islet preservative solution comprising 25 to 50 mM D-mannitol, 80 to 120 mM K-lactobionate and 15 mM $KH_2PO_4$.

6. A pancreatic islet preservative solution as recited in claim 5 further comprising 1 to 5 mM $MgSO_4$, 0 to 30,000 units/l superoxide dismutase and 0 to 5 mM nicotinamide.

7. A method of preserving pancreatic islets comprising:
    suspending isolated pancreatic islets in a solution comprising D-mannitol, at least about 80 mM K-lactobionate and a buffer; and
    storing the suspended pancreatic islets at a temperature between 0° to 15° C. until required.

8. A method as recited in claim 7 wherein the solution further comprises a membrane stabilizer, a radical scavenger and nicotinamide.

9. A method as recited in claim 8 wherein the membrane stabilizer is $MgSO_4$ and the radical scavenger is superoxide dismutase.

10. A method as recited in claim 7 wherein the buffer is $KH_2PO_4$.

11. A method as recited in claim 7 wherein the solution comprises 25 to 50 mM D-mannitol, 80 to 120 mM K-lactobionate and 15 mM $KH_2PO_4$.

12. A method as recited in claim 7 wherein the solution further comprises 1 to 5 mM $MgSO_4$, 0 to 30,000 units/l superoxide dismutase and 0 to 5 mM nicotinamide.

* * * * *